United States Patent
Gürtler et al.

(12)

(10) Patent No.: US 6,235,925 B1
(45) Date of Patent: May 22, 2001

(54) PROCESS FOR SYNTHESIZING KHI-SUBSTITUTED RING SYSTEMS

(75) Inventors: Christoph Gürtler, Köln; Manfred Jautelat, Burscheid; Helmut Greiving, Leverkusen; Herbert Hugl, Gladbach, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/386,829

(22) Filed: Aug. 31, 1999

(30) Foreign Application Priority Data

Sep. 3, 1998 (DE) .............................................. 198 40 108

(51) Int. Cl.$^7$ ........................ C07C 269/06; C07C 231/12
(52) U.S. Cl. ........................................... 560/115; 564/217
(58) Field of Search ............................. 560/115; 564/217

(56) References Cited

U.S. PATENT DOCUMENTS 5,312,940 5/1994 Grubbs et al. ....................... 556/136

FOREIGN PATENT DOCUMENTS 1-2611354 10/1989 (JP) .

OTHER PUBLICATIONS

Tetrhaedron Letters, vol. 34, No. 41, (month unavailable) 1993, pp. 6619–6622, Roshan Jumnah and Jonathan M.J. Williams, Synthesis of N–Protected Amino Esters via Palladium Catalysed Allylic Substitution.

J. Chem. Soc., Perkin Trans, 1, (month unavailable) 1997, pp. 1411–1420, Justin F. Bower, Roshnan Jumnah, Andrew C. Williams and Jonathan M.J. Williams, Palladium–catalysed asymmetric allylic substitution: synthesesis of α–and β–amino acids.

J. Chem. Soc. Perkin Trans 1 (month unavailable) 1993, pp. 2429–2432, Yoshiyasu Ichikawa, Masatugu Yamazaki and Minoru Isobe, Novel, Resgioselective Allylamine Construction; First Synthesis of Geranyllinaloisocyanide, a Diterpene from the Marine Sponge, Halichondria Sp. (1993).

J. Chem. Soc., Perkin Trans. 1, (month unavailable) 1997, pp. 1449–1455. Yoshiyasu Ichikawa, Masafumi Osada, Ikuko I. Ohtani and Minoru Isobe, A new synthetic method for the preparation of amino sugars through an allyl cyanate–to–isocyanate rearrangement.

Synlett, Nov. 1990, pp. 677–679, Pavel Kočovsky, A Facile Method for the preparation of Primary Allylic Amines from the Oximes of a α,β–Unsaturated Ketones.

J. Am. Chem. Soc. (month unavailable) 1991, 113, pp. 7195–7205, Yihui Yang, Francois Diederich, and Joan Selverstone Valentine, Lewis Acidic Catalysts and Olefin Expoxidation by Iodosylbenzene.

J. Am. Chem. Soc. (month unavailable) 1990, 112, pp. 7826–7828, Yihui Yang, Francois Diederich, and Joan Selverstone Valentine, Reaction of Cyclohexene with Iodosylbenzene Catalyzed by non–Porphyrin Complexes of Iron(III) and Aluminum(III). Newly Discovered Products and a New Mechanistic Proposal.

Journal of the American Chemical Society, 94:22, Nov. 1, 1972, pp. 7892–7898, Tatsuya.

Shono and Akihiko Ikeda, Electrooganic Chemistry. X. Anodic Allylic Substitution.

J.C.S. Chem. Comm., (month unavailable) 1981, pp. 546–547, Akio Toshimitsu, Hiroto Owada.

Toshiaki Aoai, Sakae Uemura and Masaya Okano, Selenoxide Fragmentation Leading to Allylic Amides.

Can. J. Chem. vol. 52, (month unavailable) pp. 3201–3205, Claude Briguet, Christian Freppel.

Jean–Claude Richer et Miklos Zador, Oxydation du cyclohexene par le nitrate cerique d'ammonium.

J. Org. Chem. (month unavailable) 1991, 56, pp. 1971–1972, Yves Leblanc, Robert Zamboni and Michael A. Bernstein, Amination of Olefinic Compounds with Bis(2,2,2–trichloroethyl) Azodicarboxylate.

J. Org. Chem. (month unavailable) 1983, 48, pp. 3561–3564, G. Kresze and H. Münsterer, Bis(methoxycarbonyl)sulfur Diimide, a Convenient Reagent for the Allylic Amination of Alkenes.

T. Prinz et al., Angew Chem. 108, (month unavailable) 1996—pp. 1835–1836, Zweiphasenkatalyse: eine Strategie zur Vermeidung von Konsekutievereaktionen am Beispiel der Telomerisation von Butadien und Amminoniak.

P. Schwab et al., J. Am. Chem. Soc. 118 (month unavailable) 1996 pp. 100–110 Synthesis and Applications of RuCl$_2$(=CHR') (PR$_3$)$_2$: The Influence of The Alkylidene Moiety on Metathesis Activity.

M. Schuster et al., Angew. Chem. 109, (month unavailable) 1997—pp. 2124–2144—Die Olefinmetathese in der Organischen.

S.K. Armstrong, J. Chem. Soc. Perkins Trans. 1, (month unavailable) 1998 pp. 371–388 Ring Closing Diene Metathesis In Organic Synthesis.

A.W. Stumpf et al. J. Chem. Soc. Chem. Commun., (month unavailable) 1995, pp. 1127–1128—Ruthenium–based Catalysts for the Ring Opening Metathesis Polymerization of Low–strain Cyclic Olefins and of Functionalised Derivatives of Norbornene and Cyclooctene.

*Primary Examiner*—Floyd D. Higel
*Assistant Examiner*—Ebenezer Sackey
(74) *Attorney, Agent, or Firm*—Joseph C. Gil; Diderico van Eyl

(57) ABSTRACT

Using the process according to the invention, it is possible to provide, with few reaction steps, a novel route to α-substituted ring systems which optionally have further substituents.

8 Claims, No Drawings

PROCESS FOR SYNTHESIZING KHI-SUBSTITUTED RING SYSTEMS

BACKGROUND OF THE INVENTION

The process according to the invention provides, with few reaction steps, a novel, advantageous route to α-substituted ring systems. These ring systems include the tetrahydroanilines. These are interesting precursors of fine chemicals or crop protection agents, since further transformations at the double bond are possible. They are furthermore a possible source for cyclohexylamine which is used as a vulcanization promoter or corrosion inhibitor and as a precursor for synthetic sweeteners (for example for cyclamate).

According to the prior art that has hitherto been disclosed, the preparation of tetrahydroanilines requires a large number of steps or partial steps: P. Kocovsky (Synlett 1990, 677) describes a route to tetrahydroaniline derivatives by reacting cyclohexenone with hydroxylamine in pyridine to give cyclohexenone oxime which is subsequently acylated in pyridine and then reduced with lithium aluminium hydride. Using this process, it is possible to obtain good yields; however, a reduction with lithium aluminium hydride is not suitable for industrial application or the preparation of large amounts.

Y. Yang, F. Diederich and J. S. Valentine (*J. Am. Chem. Soc.* 1991, 113, 7195 and *J. Am. Chem. Soc,* 1990, 112, 7826) describe the oxidation of cyclohexene with iodosylbenzene in the presence of aluminium triflate and acetonitrile in yields of at most 13%. T. Shono and A. Ikeda (*J. Am. Chem. Soc.* 1972, 94, 7892) disclose the electrooxidation of cyclohexene in acetonitrile with small amounts of water; however, they obtain the desired tetrahydroaniline derivative only as by-product. They do not state the yield. T. Toshimitsu, H. Owada, T. Aoai, S. Uemura and M. Okana (*J. C. S, Chem. Commun.* 1981, 546) carry out a hydrogen peroxide oxidation of α-selenylphenyl-acetamidocyclohexane and obtain, at temperatures of 250° C., the desired tetrahydroaniline derivative in very good yields, but with the aid of selenium, which is difficult to use industrially.

R. Jumnah, M. J. Williams, A. C. Williams (*Tetrahedron Letters* 1993, 34, 6619) and J. F. Bower, R. Jumnah, A. C. Williams, J. M. J. Williams (*J. Chem. Soc., Perkin Trans.* 1 1997, 1411) describe a process for preparing a tosylated tetrahydroaniline derivative by reacting, with palladium catalysis, O-acyl-2-cyclohexenol with tosylamide. Also described is a route starting from O-acetyl-2-cyclohexenol via palladium-catalysed reaction with an azide ion to give azido-2-cyclohexene and subsequent transformation of the azide with thioacetic acid to give acetamido-2-cyclohexene in an overall yield of 46%. These processes involve a high number of steps, and they sometimes use starting materials (azide) which are difficult to handle.

Y. Ichikawa, M. Yamazaki, M. Isobe (*J. Chem. Soc. Perkin Trans.* 1, 1993, 2429) and Y. Ichikawa, M. Osuda, I. I. Ohtani, M. Isobe (*J. Chem. Soc., Perkin Trans.* 1 1997, 1449) describe a process where initially 2-cyclohexenol is reacted with trichloroacetyl isocyanate and potassium carbonate to give O-carboxyamide-2-cyclohexenol which, in a subsequent step, is dehydrated to give O-cyano2-cyclohexenol which in turn is rearranged to give 2-cyclohexenyl isocyanate in good yields. This 2-cyclohexenyl isocyanate is then rearranged with trimethylaluminium to give the desired tetrahydroaniline derivative. It is particularly disadvantageous here that stoichiometric amounts of trichloroacetyl isocyanate and trimethylaluminium, which is difficult to handle in this rearrangement, are required.

C. Briguet, C. Freppel, J.-C. Richer and M. Zador (*Can. J. Chem.* 1974, 52, 3201) describe a process for the oxidation of cyclohexene with cerium ammonium nitrate in acetonitrile which contains 1% of water, and they obtain acetamido-2-cyclohexene. Here, the use of stoichiometric amounts of cerium ammonium nitrate stands in the way of industrial use. Y. Leblanc, R. Zamboni, M. A. Bernstein (*J. Org. Chem.* 1991, 56, 1971) describe an ene reaction of cyclohexene with bis-(2,2,2-trichloroethyl) azodicarboxylate at 155° C. which, after work-up, affords a yield of 70% of the desired tetrahydroaniline derivative.

G. Kresze and H. Münsterer (*J. Org. Chem.* 1983, 48 3561) describe an ene reaction of cyclohexene with bis (methoxycarbonyl)sulphurdiimide to give a product which, after basic work-up, affords a tetrahydroaniline derivative. In the last two cases, the fact that the reagent has to be used in stoichiometric amounts stands in the way of commercial utilization.

JP-A-01 261 354 (Sumitomo Corp.) describes the best industrial process for the synthesis of tetrahydroaniline derivatives that has hitherto been disclosed. In an autoclave, 1,2-dichlorohexane is reacted in the presence of ammonia in isopropanol to give 2-cyclohexeneamine in a yield of 80%. However, the fact that it is necessary to obtain 1,2-dichlorohexane first, and the high expense in apparatus for carrying out autoclave reactions make this process appear to be not particularly advantageous.

There was therefore a need for a simpler route to tetrahydroaniline, providing a considerable relief for the environment and simultaneously reducing production costs.

DESCRIPTION OF THE INVENTION

This object is achieved according to the invention by a ring closure metathesis reaction which, starting from terminal 3-amino-octadienes, leads to the corresponding ring-closed compounds. Such a ring closure metathesis reaction has hitherto not been disclosed.

It was another object of the present invention to provide a universally applicable process which, in addition to tetrahydroaniline, provides access also to other, optionally larger, α-functionalized unsaturated ring systems of the formula (II).

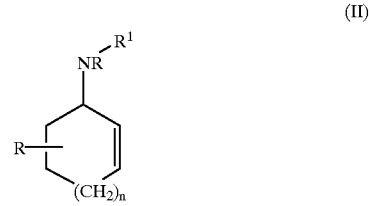

(II)

In the olefin metathesis of functionalized terminal dienes in the presence of noble metal catalysts, a ring closure of the diene is induced, and ethylene is obtained as a further product of value in this reaction (a review of this reaction type is given, for example, in M. Schuster, S. Blechert, *Angew. Chem.* 1997, 109, 2124 and S. Armstrong, *J. Chem. Soc., Perkin Trans.* 1, 1998, 371). The dienes required as starting materials can easily be obtained by a so-called telomerization reaction or by other reaction routes known per se.

The telomerization reaction (described, for example, by T. Prinz, W. Keim, B. Drieben-Hölscher in *Angew. Chem.*

1996, 108, 1835) uses starting materials which are very simple and obtainable in an easy manner, i.e. ammonia and butadiene.

According to the invention, this starting material is preferably employed in a protected form, particularly preferably in its acylated form. In general, the formamide will be used, but it is also possible to use other protective groups, such as carbamates. The protective groups can be removed easily or transferred to the starting material in an equilibrium reaction, so that this auxiliary can be recycled completely.

Preferred catalysts for use in the process according to the invention are the ruthenium alkylidene compounds described in WO-A-93/20111, the ruthenium-based catalyst systems described by A. W. Stumpf, E. Saive, A. Deomceau and A. F. Noels in *J. Chem. Soc., Chem. Commun.* 1995, 1127–1128 or the catalyst systems published by P. Schwab, R. H. Grubbs and J. W. Ziller in *J. Am. Chem. Soc.* 1996, 118, 100.

Particular preference is given to using bis(tricyclohexylphosphine)benzylideneruthenium(IV) dichloride.

From an α-functionalized diene, preferably a 1,7-octadiene but also a longer-chain diene, the process according to the invention quantitatively gives a cyclic unsaturated ring system of the formula (II).

In a preferred embodiment of the invention, the operations are carried out under a permanent atmosphere of protective gas, so that the catalyst can be used for a plurality of cycles.

The amount of catalyst used in the process according to the invention is generally at from 0.001 to 10 mol%, based on the compound of the formula (I), and the reaction is preferably carried out at from 0.1 to 1 mol%.

The reaction time varies and depends on the reaction temperature, the reaction pressure and the type and the amount of the catalyst. Usually, the reaction time is from 0.01 to 30 hours, preferably from 1 to 10 hours.

The presssure to be used in the process according to the invention is not a critical parameter. It is possible to reduce the pressure to 0.01 bar and to apply pressures of up to 100 bar, for example. However, preference is given to an absolute pressure of from 0.1 to 10 bar, particularly preferably to atmospheric pressure.

The process according to the invention permits the ring closure metathesis to be carried out in a solvent or without the use of a solvent. The solvent can be employed effectively for controlling the rate of reaction. The solvent which is suitable for a chosen substrate can be determined in each specific case by a person skilled in the art without great expenditure in a customary serial test. The solvent is preferably an inert organic solvent, for example aliphatic hydrocarbons having 4 to 20 carbon atoms which are liquid under reaction conditions, such as butane, pentane, hexane or heptane, chlorinated or brominated hydrocarbons, for example dichloromethane, chloroform, bromoform, iodoform, or else chlorinated or brominated benzenes, or aromatic hydrocarbons, such as benzene, toluene or xylene, where these are to be understood as just being examples. In addition, it is also possible to use ethers (for example diphenyl ether). Preference is given to using benzene or toluene.

The reaction temperature is not a critical parameter. In general, the reaction temperature is determined by the boiling point of the solvent used, or by the boiling points of the starting materials, unless the action of pressure works against this.

General Reaction Equation of the Process

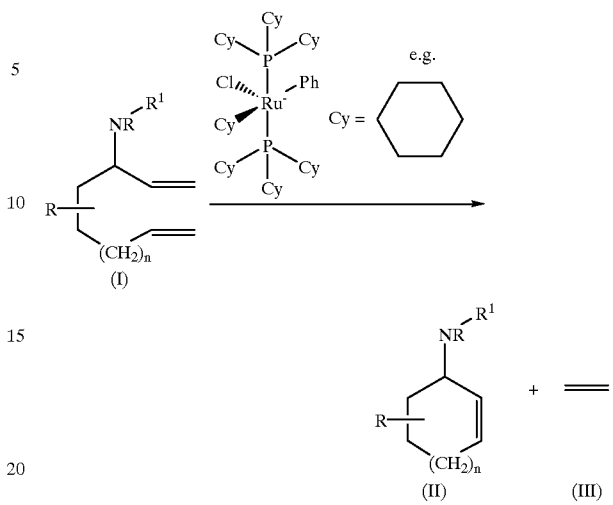

Here, in each case independently of one another,

R represents one or more further organic substituents, preferably optionally fused aryl, alkyl, —CN, —COOR$^2$ or preferably hydrogen or halogen, R$^1$ represents —COR$^2$, —SO$_2$PhR$^2$, —COOR$^2$, CONRR$^2$, CONRR, tert-butyl, PR$_2$ or PR$^2$$_2$, hydrogen or R which is bound to the nitrogen in formula (II) and R$^1$ form together a cyclic residue

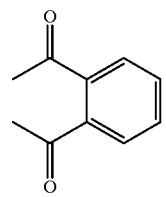

R$^2$ represents alkyl, aryl, preferably phenyl or hydrogen and n represents the numbers 1, 2, 3 or 4, preferably 1 or 2, particularly preferably 1.

It is also possible for the double bond of the resulting molecule (II) to be substituted by at least one radical R.

The nature of the substituent R is not essential for the invention; in principle, it is possible to use all the radicals which are customary in organic chemistry. Preferred alkyl groups R according to the invention are linear or branched C$_1$- to C$_8$-alkyl groups, particularly preferably linear C$_1$- to C$_4$-alkyl groups, and the aryl groups are preferably phenyl groups.

The invention provides valuable advantages to the industry. Since the invention uses a simpler route to tetrahydroaniline, the invention provides a considerable relief for the environment and simultaneously reducing production costs. Such a direct production of tetrahydroaniline is especially valuable because tetrahydroanilines are precursors of fine chemicals and crop protection agents. Further, tetrahydroanilines are a possible source for cyclohexylamine, a vulcanization promoter or corrosion inhibitor. Tetrahydroanilines are also precursors for synthetic sweeteners (for example for cyclamate). The benefits of the invention, however, are not limited to the making of tetrahydroanilines. In addition, the process provides a universally applicable process for making compounds other than tetrahydroaniline, the invention provides access also to other, optionally larger, α-functionalized unsaturated ring systems of the formula (II).

The invention is further illustrated but is not intended to be limited by the following examples in which all parts and percentages are by weight unless otherwise specified.

EXAMPLES

Example 1: N-acetyl-3,4,5,6-tetrahydroaniline

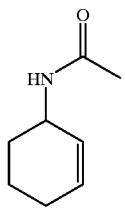

In a Schlenk tube, which has been dried thoroughly by heating, 176 mg (1 mmol) of N-acetyl-3-amino-1,7-octadiene and 7 mg of bis(tricyclohexylphosphine)benzylideneruthenium(IV) dichloride (about 1 mol%) are dissolved in 2 ml of abs. benzene under an atmosphere of argon. The mixture is allowed to react at 80° C. for approximately 14 h. For work-up, the mixture is filtered through a very short silica gel filtration column (0.5 cm) (mobile phase: ether) and the filtrate is concentrated. Yield: 138 mg of N-acetyl-3,4,5,6-tetrahydroaniline (0.99 mmol, 99%). $R_f$ value (mobile phase: petroleum ether ethyl acetate 2:1, stationary phase (TLC): $SiO_2$): 0.22;
$^1$H-NMR (400 MHz, $CDCl_3$) δ=5.85 (1H, d, J=9.0 Hz), 5.60 (1H, m), 5.58 (1H, d, J=9.0 Hz), 4.48 (1H, m), 2.00 (2H, m), 1.95 (3H, s), 1.91 (1H, dddd, J=12.0, 11.0, 6.0, 6.0 Hz), 1.65 (2H, tt, J=6.0, 6.0 Hz), 1.55 (1H, dddd, J=12.0, 11.0, 6.0, 6.0 Hz).

Example 2: N-carboxymethyl-3,4,5,6-tetrahydroaniline

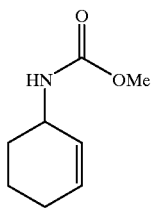

In a Schlenk tube, which has been dried thoroughly by heating, 92 mg (0.5 mmol) of N-carboxymethyl-3-amino-1,7-octadiene and 4 mg of bis(tricyclohexylphosphine)benzylideneruthenium(IV) dichloride (about 1 mol%) are dissolved in 1 ml of abs. benzene under an atmosphere of argon. The mixture is allowed to react at 80° C. for approximately 14 h. This reaction also proceeds, with the same result and in the same period of time, in chloroform (b.p. 56° C.). For work-up, the mixture is filtered through a very short silica gel filtration column (0.5 cm), and the filtrate is then washed four times with 1 ml of acetonitrile each time and concentrated. Yield: 77 mg of N-carboxymethyl-3,4,5,6-tetrahydroaniline (0.49 mmol, 99%).
$^1$H NMR (400 MHz, $CDCl_3$) δ 5.85 (1H, d, J=9.0 Hz), 5.60 (1H, d, J=9.0 Hz), 4.70 (1H, s), 4.20 (1H, s), 3.65 (3H, s), 1.98 (2H, m), 1.90 (1H, m), 1.62 (2H, m), 1.52 (1H, m).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for preparing a α-substituted ring system of the formula (II)

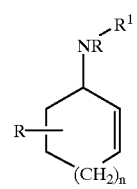

wherein, in each case independently of one another,
R is one or more organic substituents,
$R^1$ is —$COR^2$, —$SO_2PhR^2$, —$COOR^2$, $CONRR^2$, CONRR, tert-butyl, $PR_2$ or $PR^2_2$, hydrogen or
R which is bound to the nitrogen in formula (II) and $R^1$ form together a cyclic group having the formula

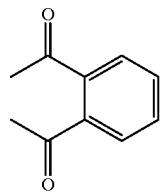

$R^2$ is alkyl, aryl,
and
n represents the numbers 1, 2, 3 or 4,
wherein the double bond is unsubstituted a substituted by at least one radical R,
which process comprises subjecting a compound of the formula (I)

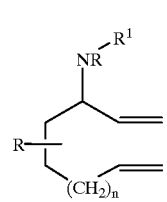

in which
R, $R^1$ and n are each as defined above, to a ring closure metathesis reaction in the presence of a noble metal catalyst.

2. Process according to claim 1, wherein the noble metal catalyst used is a ruthenium complex.

3. Process according to claim 1, wherein the noble metal complex is bis(tricyclohexylphosphine)benzylideneruthenium(IV) dichloride.

4. Process according to claim 1, wherein R in the formulae (I) and (II) comprises hydrogen, optionally fused aryl, alkyl, —CN, —$COOR^2$ or halogen.

5. Process according to claim 1, wherein n in the formulae (I) and (II) represents 1 or 2.

6. Process according to claim 1, wherein n in the formulae (I) and (II) represents 1.

7. Process according to claim 1, wherein in the formulae (I) and (II) $R^1$ and R each comprise hydrogen and n represents 1.

8. The process of claim 1, wherein $R^2$ is phenyl.

* * * * *